United States Patent
Zeng et al.

(10) Patent No.: US 6,627,893 B1
(45) Date of Patent: Sep. 30, 2003

(54) FOCUSED ROTATING SLAT-HOLE FOR GAMMA CAMERAS

(75) Inventors: Gengsheng Lawrence Zeng, Sandy, UT (US); Daniel Gagnon, Twinsburg, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 150 days.

(21) Appl. No.: 09/808,935

(22) Filed: Mar. 15, 2001

(51) Int. Cl.[7] .............................................. G01T 1/166
(52) U.S. Cl. .......................... 250/363.04; 250/363.08; 250/363.1
(58) Field of Search ........................ 250/363.1, 363.04, 250/363.08

(56) References Cited

U.S. PATENT DOCUMENTS

| | | | |
|---|---|---|---|
| 4,090,080 A | 5/1978 | Tosswill | 250/366 |
| 4,262,207 A | 4/1981 | Tosswill | 250/366 |
| 4,476,389 A * | 10/1984 | Ueyama et al. | 250/363.05 |
| 4,559,597 A | 12/1985 | Mullani | 364/414 |
| 4,982,096 A | 1/1991 | Fujii et al. | 250/367 |
| 5,077,770 A | 12/1991 | Sammon | 378/101 |
| 5,245,191 A * | 9/1993 | Barber et al. | 250/363.04 |
| 5,404,293 A * | 4/1995 | Weng et al. | 378/15 |
| 5,430,297 A * | 7/1995 | Hawman | 250/363.1 |
| 5,481,115 A | 1/1996 | Hsieh et al. | 250/363.04 |
| 5,554,848 A * | 9/1996 | Hermony et al. | 250/363.05 |
| 5,565,684 A | 10/1996 | Gullberg et al. | 250/363.04 |
| 5,847,398 A * | 12/1998 | Shahar et al. | 250/370.09 |
| 5,967,983 A | 10/1999 | Ashburn | 600/436 |
| 5,991,357 A | 11/1999 | Marcovici | 378/19 |
| 6,046,454 A | 4/2000 | Lingren et al. | 250/370.01 |
| 6,055,450 A | 4/2000 | Ashburn | 600/431 |
| 6,091,070 A | 7/2000 | Lingren et al. | 250/370.09 |
| 6,242,743 B1 * | 6/2001 | DeVito et al. | 250/363.05 |
| 6,256,369 B1 | 7/2001 | Lai | 378/14 |

2002/0130265 A1 * 9/2002 Zerg et al. ............. 250/363.04

FOREIGN PATENT DOCUMENTS

| | | |
|---|---|---|
| DE | 10010588 A1 | 5/2000 |
| WO | WO 97/43667 A1 | 11/1997 |
| WO | WO 00/38197 | 6/2000 |

OTHER PUBLICATIONS

G.L. Zeng, et al. "Eigen Analysis of Cone–Beam Scanning Geometries". *Three–Dimensional Image Reconstruction in Radiation and Nuclear Medicine* © 1996 by Kluwer Academic Publishers, Netherlands. pp. 75–86 (Conf. Jul. 1995).
G.L. Zeng, et al. "A cone beam tomography algorithm for orthogonal circle–and–line orbit". *Phys. Med. Biol.*, 1992, vol. 37, No 3, 563–577, Mar.
S. Webb, et al., "Monte Carlo modelling of the performance of a rotating slit–collimator for improved planar gamma–camera imaging," *Phys. Med. Biol.*, vol. 37, No. 5, 1095–1108, 1992, May.
Mauderli, et al., A Computerized Rotating Laminar Radionuclide Camera, *J. Nucl. Med*, 20:341–344 (1979), Apr.

(List continued on next page.)

*Primary Examiner*—Constantine Hannaher
(74) *Attorney, Agent, or Firm*—Fay, Sharpe, Fagan, Minnich & McKee, LLP

(57) ABSTRACT

γ-ray emissions (14) are detected by a rotating, one-dimensional detector array (18). Slats of a convergent or divergent collimator (16) are mounted between detector elements. The slats are canted by an angle α from focusing on a focal spot (40) on a perpendicular bisector to the detector array. As a detector head (30) revolves around a longitudinal axis (36) of the subject, the head is canted (FIG. 5) to generate angularly offset data sets. Data sets with the detector array rotated to 180° opposite orientations are processed (62) to generate a first derivative data set. Parallel lines or planes (64) of the canted data sets are processed (68) to generate a second derivative data set which is back-projected (70) in accordance with the Radon transform into a three-dimensional image representation.

20 Claims, 7 Drawing Sheets

OTHER PUBLICATIONS

Entine, et al., "Cadmium Telluride Gamma Camera," *IEEE Transactions on Nuclear Science*, vol. NS–26, No. 1:552–558 (1979), Feb.

Urie, et al., "Rotating Laminar Emission Camera with GE–detector Experimental Results:" *Med. Phys.* 8(6):865–870 (1981), Nov.–Dec.

Mauderli, et al., "Rotating Laminar Emission Camera with GE–Detector: An Analysis," *Med. Phys.* 8(6)871–876 (1981), Nov.–Dec.

Malm, et al., "A Germanium Laminar Emission Camera," *IEEE Transactions on Nuclear Science*, vol. NS–29, No. 1:465–468 (1982), Feb.

Mauderli, et al., "Rotating Laminar Emission Camera with GE–Detector: Further Developments," *Med. Phys.* 14(6):1027–1031 (1987), Nov.–Dec.

Wagner, et al., "3–D Image Reconstruction From Exponential X–Ray Projections Using Neumann Series", 2001 IEEE Int. Conf. on Acoustics, Speech & Signal Processing, May 7–11, 2001, pp. 2017–2020 XP001084148, Salt Lake UT US p2017.

* cited by examiner

FOCUSED ROTATING SLAT-HOLE FOR GAMMA CAMERAS

BACKGROUND OF THE INVENTION

The present invention relates to the diagnostic imaging arts. It finds particular application in conjunction with SPECT nuclear imaging systems and will be described with particular reference thereto. It will be appreciated, however, that the present invention is useful in conjunction with other systems that utilize collimated detectors to detect penetrating radiation, and is not limited to the aforementioned application.

In nuclear imaging, a source of radioactivity is used to provide non-invasive diagnostic images. The source is typically injected into a patient, although external sources are also utilized. Radiation from the source traverses at least a portion of the patient and is detected by radiation detectors.

Typically, a nuclear camera has one, two, or three detector heads. In rotating laminar emission cameras (ROLEC), a one-dimensional detector array or line of detectors is rotated in each head. Collimator vanes which are mounted between the detectors of the array rotate with the detector array. In rotating laminar emission cameras, the one-dimensional collimation results in a plane integral reconstruction as opposed to a line integral reconstruction, as is typical in most Anger camera systems. This distinction illustrates a particular difference between one-dimensional and two-dimensional collimation. In a system collimated in one dimension, the detector "sees" that is, receives radiation from, a plane. In a typical Anger camera with two dimensional collimation, each collimated element of the detector sees a line of the imaging volume. Moreover, described more accurately, the typical ROLEC produces only an approximation of a planar integral.

In actuality, the plane integral should have a weighting factor included therein in order to compensate for a 1/r dependence to an object being imaged, where r represents the distance of a detectable radiation event to the detector. All other things being equal, the detector is more sensitive to relatively close objects, and is less sensitive to relatively distant objects. Typically, previously developed ROLECs ignore the 1/r weighting, accepting that the detected information is an approximation. Ultimately, failure to model the dependence, or improper modeling of the dependence reduces resultant image quality.

The applicants earlier copending application Ser. No. 09/708,960 discloses a reconstruction system which corrects for the 1/r dependence. The parallel collimator vanes are skewed a few degrees from perpendicular. When the detector array is rotated to 180° opposite orientations, a pair of corresponding data sets are generated whose planes are offset by a very small but known angle. As explained in detail in the aforesaid copending application, this relationship enables the 1/r dependency to be reduced to a trigonometric function of the angle, which is a constant.

Unfortunately, these relationships were limited to substantially parallel collimator geometries. Like earlier ROLEC reconstructions, data from magnifying (converging) collimators and minifying (diverging) collimators could not be reconstructed accurately.

The present invention provides a new and improved method and apparatus that overcomes the above referenced problems and others.

SUMMARY OF THE INVENTION

In accordance with one aspect of the present invention, a method of diagnostic imaging is provided. A radioactive isotope is introduced into a subject in an imaging region. The radiation is detected by a rotating solid state detector array generating a plurality of planar images. The detector array is moved about a longitudinal axis of the subject. The detector array is collimated by a non-parallel slat collimator in either a convergent or divergent formation. The detected photon emissions are reconstructed into an image representations of the subject.

In accordance with another aspect of the present invention, a diagnostic imaging apparatus is given. A means for detecting detects radiation that is transmitted through at least a portion of a subject in an imaging region. A collimating means collimates the radiation. A first rotating means rotates the detecting means about an axis perpendicular to a main longitudinal axis of the subject. A second rotating means rotates the detecting means about the longitudinal axis. A means for reconstructing reconstructs the detected radiation into an image representation.

In accordance with another aspect of the present invention, a SPECT camera is provided. A detector head that includes a linear array of detector elements and a magnifying collimator is mounted for movement about an axis of a subject. A motor rotates the array around a detector axis of rotation. A reconstruction processor reconstructs signals from the detector into an image representation.

In accordance with another aspect of the present invention, a method of nuclear imaging is provided. A linear detector array and a convergent collimator are rotated about a detector axis of rotation and around a subject axis of rotation. Radiation from the subject is converted into electrical signals which are reconstructed to form a magnified image representation.

One advantage of the present invention resides in a magnifying detector assembly.

Another advantage resides in sub-millimeter resolution.

Another advantage of the present invention is that it presents a small, relatively light nuclear detector array.

Yet another advantage is that it presents a solid state nuclear detector array.

A further advantage resides in minifying collimation with accurate reconstruction.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION IF THE PREFERRED EMBODIMENT

Figure 1:
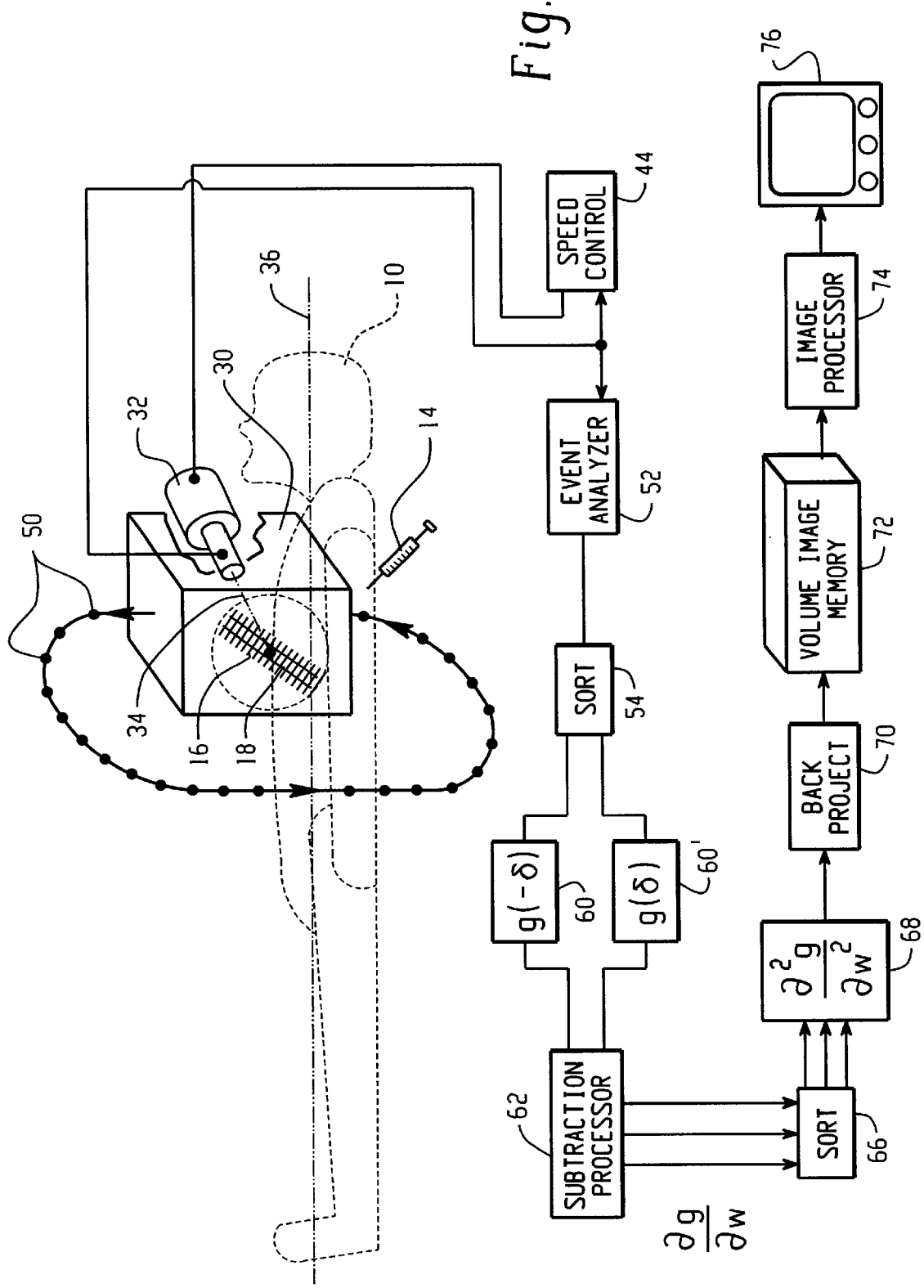
FIG. 1 is a diagrammatic illustration of a nuclear imaging device in accordance with the present invention.

With reference to FIG. 1, a region of interest of a subject 10 is disposed in an imaging region 12. In the preferred embodiment, a radiopharmaceutical 14 is injected into the subject, near a region to be imaged. For example, if a physician wants to view a blockage in the aorta, the isotope is injected into the bloodstream upstream from the blockage. As another example, the radiopharmaceutical 14 is injected into the circulatory system and its selective absorption by tissue of interest is monitored.

Atomic nuclei of the radioactive isotope decay over time. Energy is released at the time of decay in the form of a radiation photon, more specifically, a γ-ray of characteristic energy.

Many of the γ-rays produced during an imaging process are lost, propagating in useless directions. However, some of the γ-rays pass through a collimator 16, thin tungsten, lead, or other high-z vanes in the preferred embodiment, and strike a detector array 18. In the preferred embodiment and with reference to FIG. 2 the detector array 18 includes a linear array of cadmium zinc telluride (CZT) crystals. When a γ-ray strikes the detector, it frees many electrons from their bonds to the detector material. These electrons are propelled across the thickness of the crystal and form an electrical pulse signal.

Figure 2:
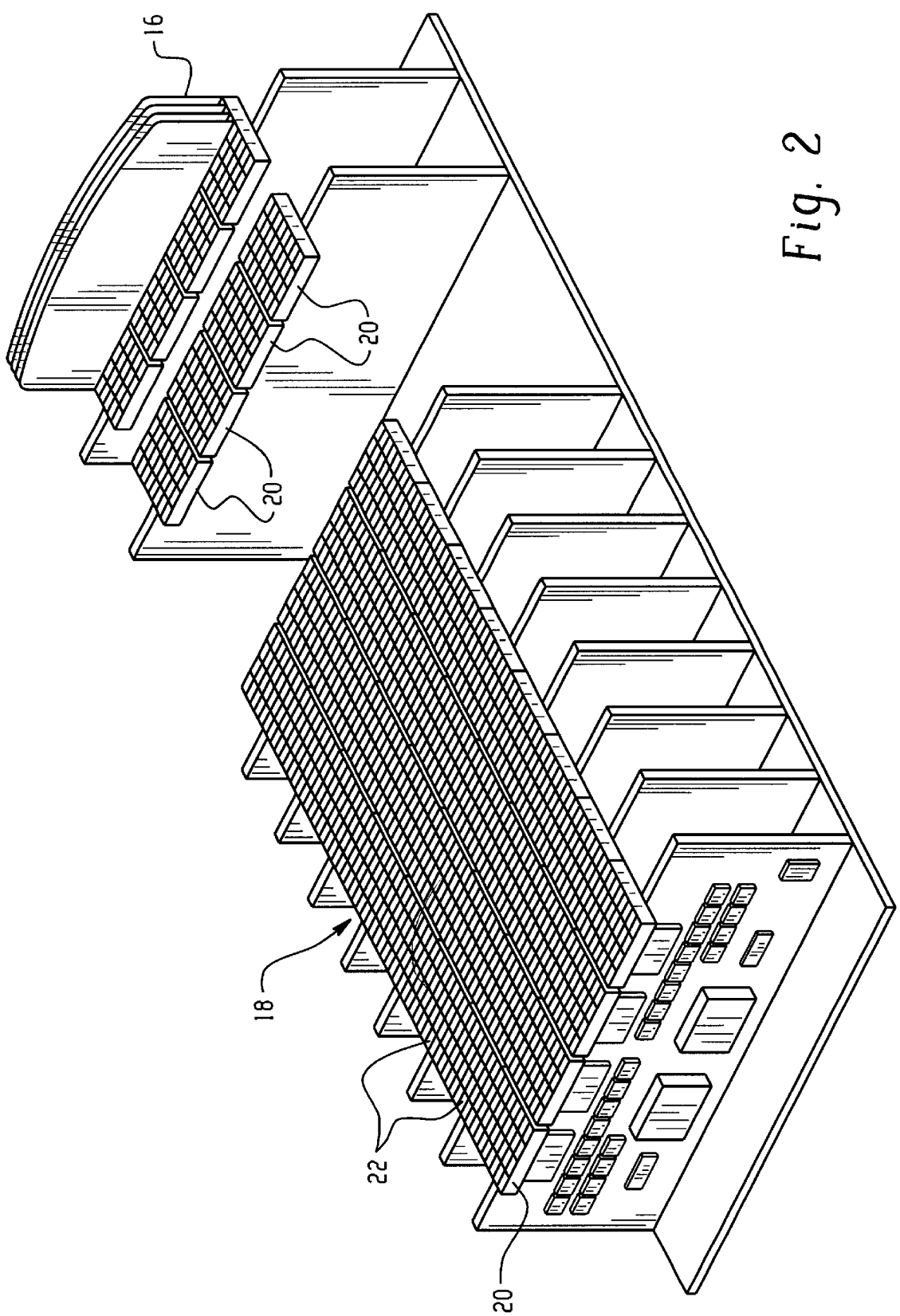
FIG. 2 is a perspective view of a detector array and collimator arrangement in accordance with the present invention.

With reference to FIG. 2, the preferred embodiment of the linear detector array 18 is defined by two dimensional detector arrays 20. The collimators 16 collimate in one dimension, and the detector array 18 is treated as one-dimensional in the direction transverse to the collimator vanes for purposes of data gathering. The detectors 22 of a single row are all sampled together as if they were a single, elongated crystal to increase photon counts.

With further reference to FIG. 1, the detector array 18 is mounted on a head 30 that is mounted to a gantry for rotation around the region of interest. In the preferred embodiment, a motor 32 rotates the detector array around an axis 34, in a plane parallel with a longitudinal axis of the patient 36. Although the detector array is illustrated as rotating around its central axis, for simplicity of illustration, more complex rotations are also contemplated. These two motions of the detector array 18, that is, rotation about its own axis and rotation of the head 30 around the subject 10 give the detector array 18 a sufficient variety of views of the subject 10 to reconstruct an accurate three-dimensional image representation.

Figure 3:
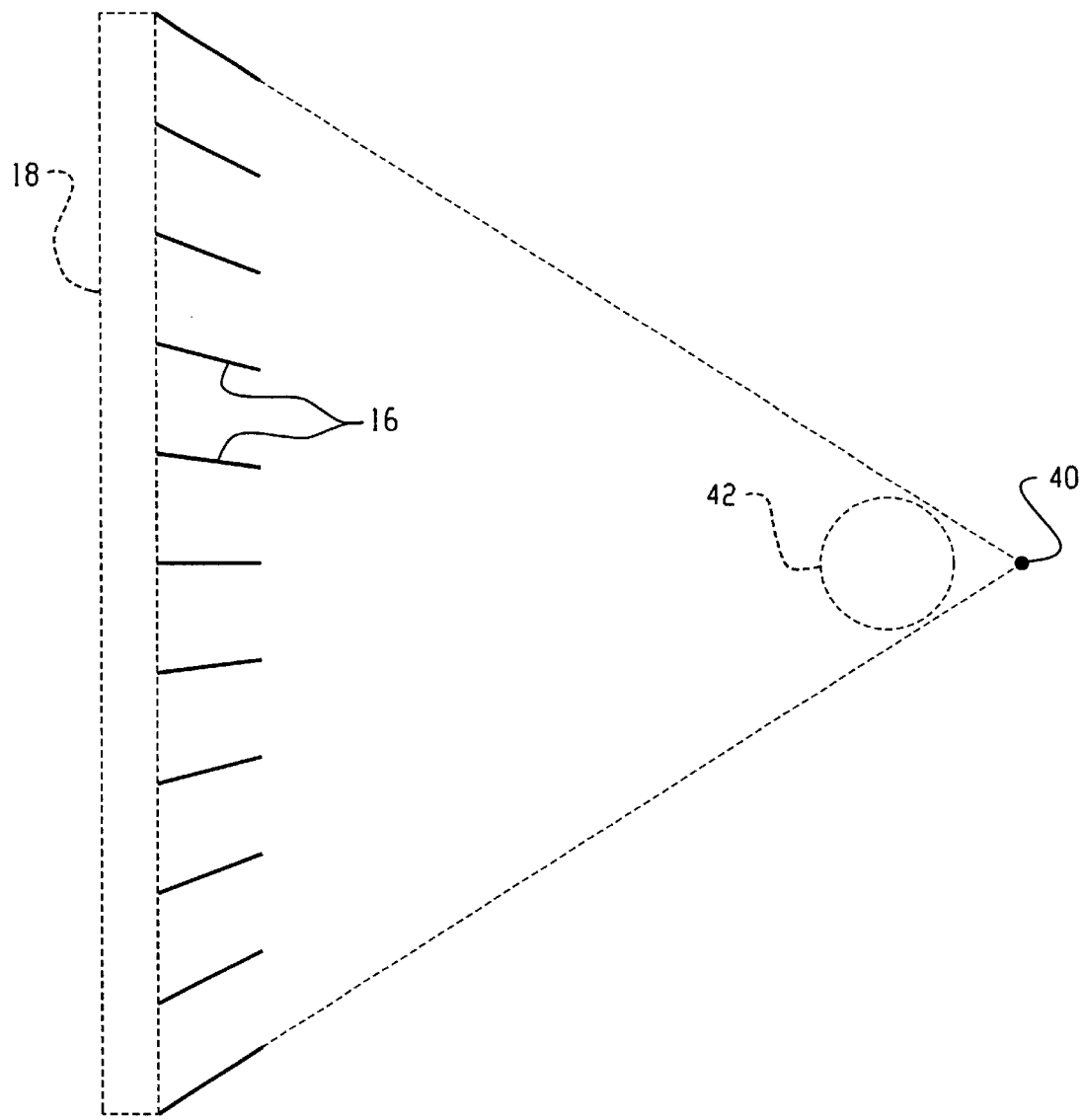
FIG. 3 is an illustration of a convergent collimated detector array, its field of view, and its focal spot, in accordance with the present invention.

With reference to FIG. 3, the slats of the collimator 16 in a magnifying embodiment are angled to converge on a focal point 40 in front of the detector. The magnifying collimator geometry uses the entire length of the detector array 18 to image a field of view 42 much smaller than itself. For example, if the detector array 18 has a length of 40 cm, and the field of view 42 has a length of 4 cm, then the field of view 42 will be imaged at ten times its normal size, that is, it will be magnified.

Figure 4A:
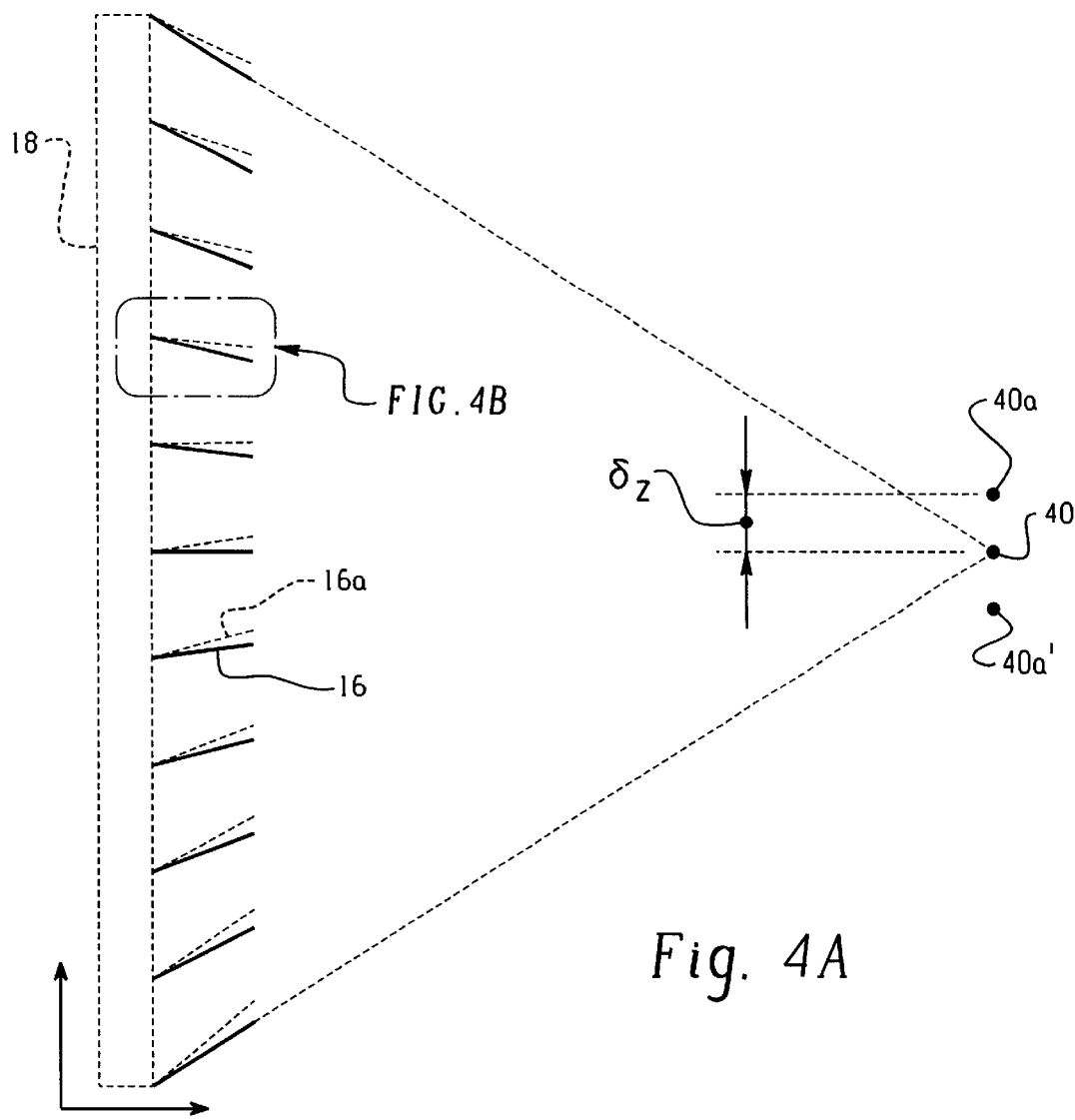
FIG. 4A is an illustration of the collimated detector array, with all of the collimator slats shifted by a uniform angle.
Figure 4B:
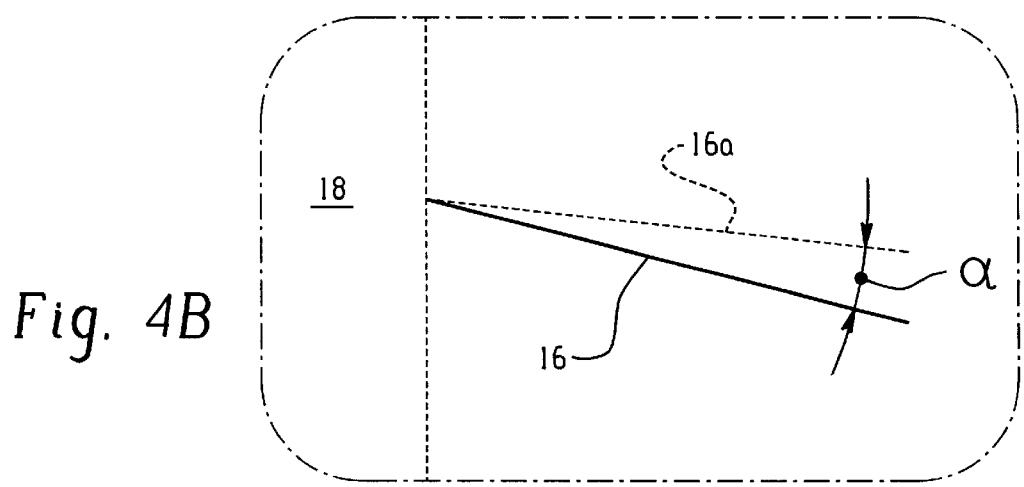
FIG. 4B is a close-up view of one of the shifted collimators slats, displaced by an angle α.

With reference to FIGS. 4a and 4b, the slats of the collimator 16 are tilted by an angle α from the convergent position described previously. The tilted collimator slats 16a converge on a shifted focal point 40a. Preferably, the angle α is greater than zero degrees and less than or equal to 5 degrees. Preferably, the angle is approximately 0.29°, but is adjusted during machine setup for optimal results in each physical environment. By tilting the collimator slats to the position 16a, the corresponding data sets collected 180° of detector rotation apart are not identical. One has the focal spot (or plane) 40a and the other the focal spot (or plane) 40a'. These two data sets can be evaluated to determine first derivative information which is used to reduce the 1/r weighting dependence discussed in the background portion above to be reduced to a constant.

With further reference to FIG. 1, an exemplary data acquisition scheme for a three-dimensional tomographic reconstruction is now discussed. Generally, data acquisition is performed using two motions. The first motion is a rotation of the detector array 18 about the axis 34 of the head 30. The second range of motion is a rotation of the head about the subject 10.

The detector array 18 is mounted on the axis 34, perpendicular to the longitudinal axis 36, with the axis 34 intersecting a center of the detector array 18. The array 18 is rotated by a motor speed control 44 about the axis, preferably through several rotations that are averaged to generate a single "SPECT view" of the subject 10. The first motion is preferably continuous, completing 360° of rotation (or multiples thereof) without stopping. The detector rotation is preferably performed while the head 30 is stationary, that is, it is performed at a single "SPECT angle" 50, from a single spot on the gantry for simplicity of explanation and data processing. However, continuous rotation of the head around the longitudinal axis produces mathematically equivalent data. The rotation of the detector generates planar projection images.

A mechanized drive moves the head 30 around the longitudinal axis, stopping at each of a plurality of the SPECT angles or sampling positions 50. The head 30 preferably traverses 180° around the subject for a single imaging cycle. Preferably, each SPECT angle 50 is separated from the next by 3°, that is, there are preferably 60 SPECT sampling angles in 180°. At each SPECT angle, the head 30 stops long enough for the detector to rotate 360°.

Figure 7:
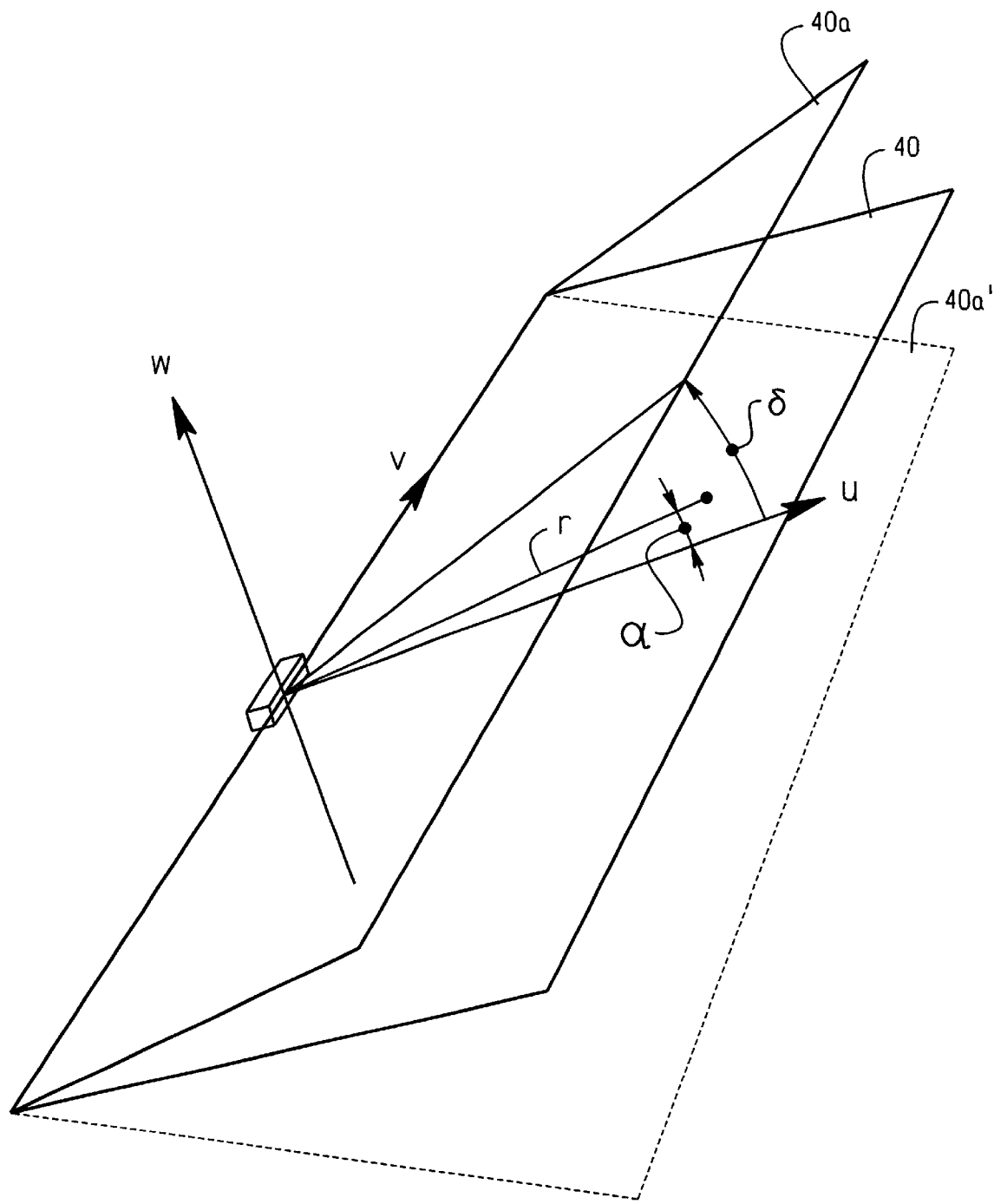
FIG. 7 is a perspective view of local coordinate systems, a cylindrical system in r, α, and ω, and a Cartesian system in u, v, and ω.

With reference again to FIGS. 4A and 4B, and a local coordinate system as shown in FIG. 7, the complementary data sets $$g(\delta) = \int \int \frac{1}{r} f(r, \alpha, r\tan\delta) \, dr \, d\alpha$$

(measured at 40a) and $$g(-\delta) = \int \int \frac{1}{r} f(r, \alpha, r\tan\delta) \, dr \, d\alpha$$

(measured at 40a') where δ is the small angle between the focal point 40 and one of the focal points 40a and 40a' are collected and stored, respectively, in memories 60 and 60'.

These two data sets are subtracted by a subtraction processor 62, and multiplied by a constant $$\frac{\cos^2\delta}{2\delta},$$

i.e.:

$$\frac{g(\delta) - g(-\delta)}{2\delta}(\cos^2\delta) = \quad (1)$$

$$\frac{\iint \frac{1}{r}f(r, \alpha, r\tan\delta)\,rdrd\alpha - \iint \frac{1}{r}f(r, \alpha, r\tan\delta)\,rdrd\alpha}{2\delta}(\cos^2\delta)$$

Equation (1) can also be expressed as:

$$\frac{g(\delta) - g(-\delta)}{2\delta}(\cos^2\delta) = \quad (2)$$

$$\iint \frac{1}{r}\frac{f(r, \alpha, r\tan\delta) - f(r, \alpha, r\tan\delta)}{2\delta}rdrd\alpha(\cos^2\delta)$$

The $$\frac{f(r, \alpha, r\tan\delta) - f(r, \alpha, -r\tan\delta)}{2\delta}$$

portion of Equation (2) will be readily recognized as an approximation of the partial derivative of f with respect to the variable δ and multiplied by a constant $$\frac{r}{\cos^2\delta}$$

$$\left(\text{because } \frac{d}{d\delta}r\tan\delta = \frac{r}{\cos^2\delta}\right).$$

When the local coordinate system of FIG. 7 is used, expression (2) becomes:

$$\iint \frac{\partial}{\partial\omega}f(r, \alpha, \omega)rdrd\alpha = \frac{\partial}{\partial\omega}\iint f(r, \alpha, \omega)rdrd\alpha \quad (3)$$

$$\frac{g(\delta) - g(-\delta)}{2\delta}(\cos^2\delta) \approx \iint \frac{\partial}{\partial\omega}f(r, \alpha, \omega)rdrd\alpha = \quad (4)$$

$$\frac{\partial}{\partial\omega}\iint f(r, \alpha, \omega)rdrd\alpha$$

Here, $\iint f(r, \alpha, \omega)\,r\,dr\,d\alpha$ is the Radon transform. The Radon inversion formula reconstructs the image f by backprojecting the second derivative of the Radon transform, i.e., by back projecting $$\frac{\partial^2}{\partial\omega^2}\iint f(r, \alpha, \omega)rdrd\alpha.$$

Figure 5:
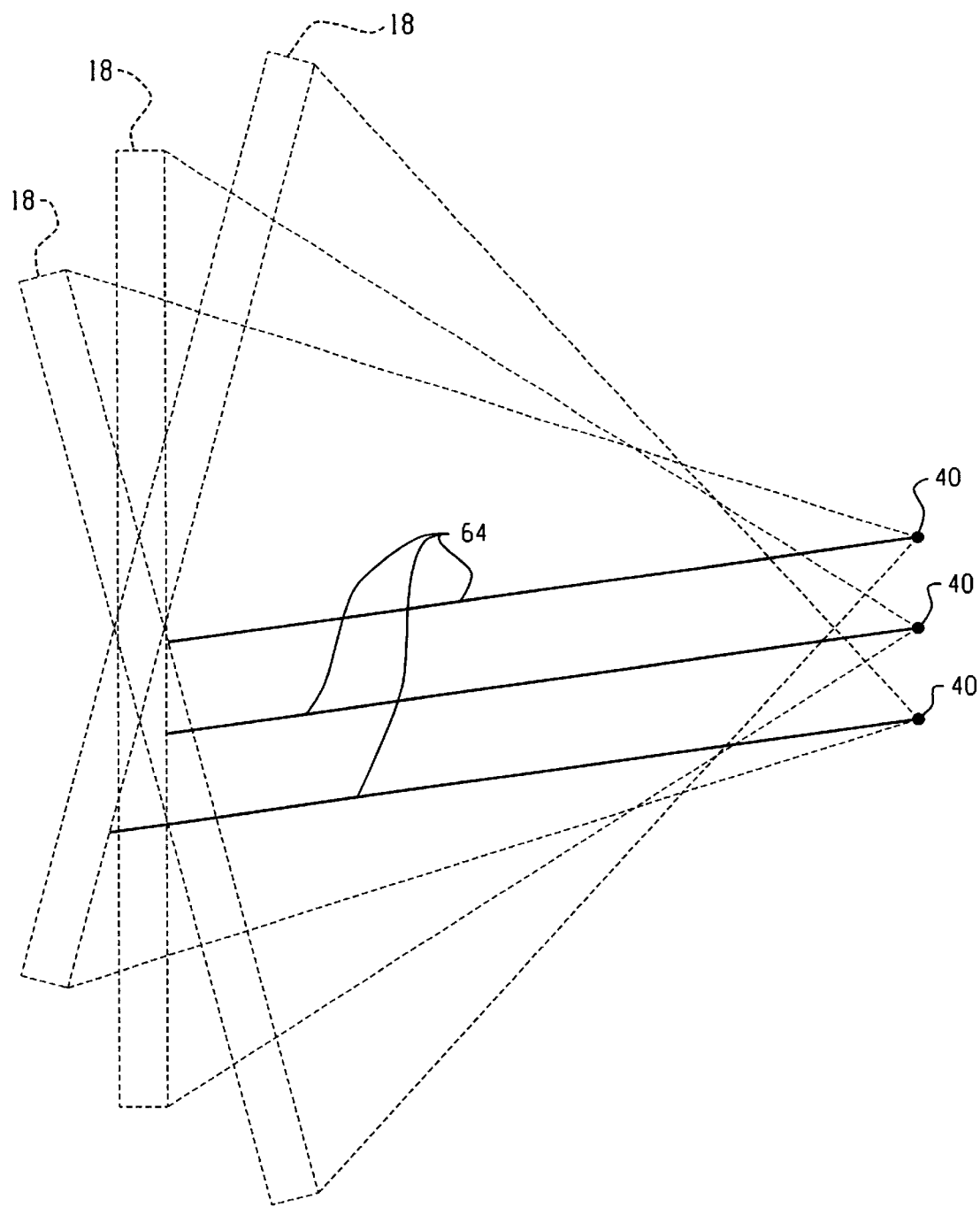
FIG. 5 is an illustration of an action of tilting the detector array to obtain parallel views of the field of view.

With reference to FIG. 5, the detector is not just rotated about its longitudinal axis, but is also wobbled. That is, the detector head is rotated at each of three angular offsets, in the preferred embodiment to create three sets of planes of first derivative data 64. These planes are sorted 66 into parallel planes. A second derivative processor 68 evaluates the parallel planes of first derivative data to generate a second derivative. A backprojector 70 backprojects the data in accordance with the Radon inversion formula into a volume image memory 72. An image processor 74 processes selected portions of the volumetric image representation to generate slice, three-dimensional rendering, projection, and other image representations as may be requested by the operator for display on a human-readable display 76 such as a computer monitor, LCD display, active matrix monitor, or the like.

Figure 6B:
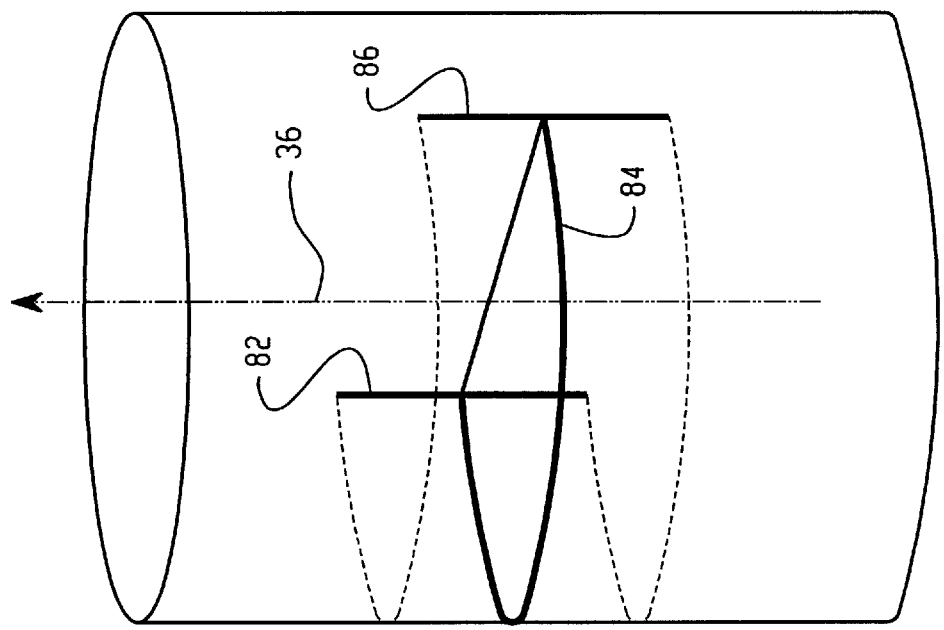
FIG. 6B is another preferred path of the focal spot about the longitudinal axis.
Figure 6A:
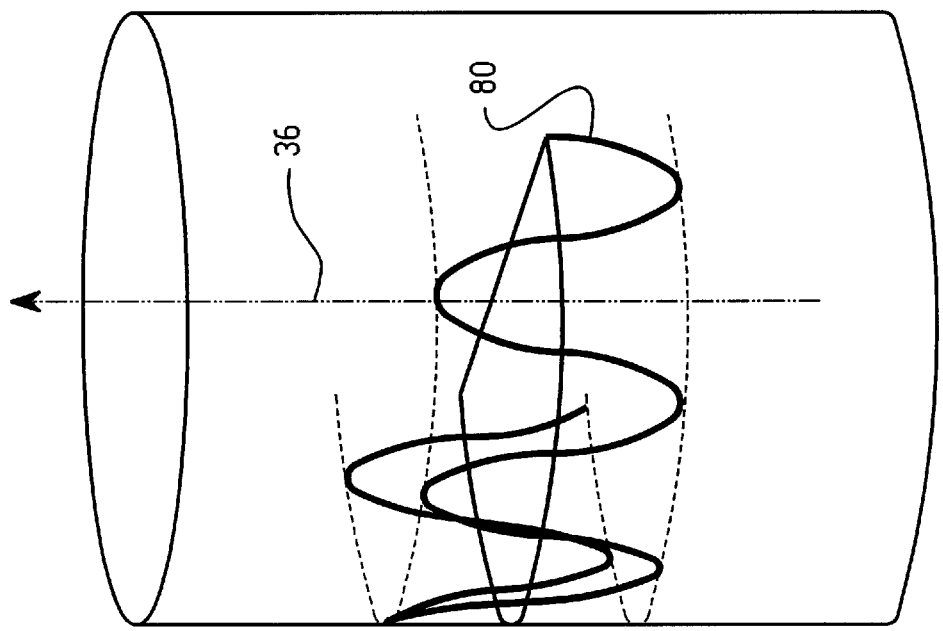
FIG. 6A is one preferred path of a magnifying collimator focal spot about a longitudinal axis of a patient.

The tipping action may be accomplished in various modes. In the embodiment of FIG. 6a, the head rotates continuously around the longitudinal axis of the subject while the detector head wobbles, such that the focal spot follows a generally sinusoidal trajectory 80. In the embodiment of FIG. 6b, the detector is wobbled at the starting point to create vertical movement of the focal spot 82. The detector head is then rotated without wobbling even in steps or continuously, such that the focal spot moves along trajectory 84, either continuously or in steps. After 180° of rotation, the detector head is again wobbled to move the focal spot along a second vertical path 86.

In an alternate embodiment, the collimator 16 is a divergent collimator making the viewable field of the detector array 18 larger than the array itself, producing a minimizing effect in the reconstructed image. The focal spot 40 in such a system would be behind the detector.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method of diagnostic imaging comprising:

a) introducing a radioactive isotope into a subject located in an imaging region;

b) rotating a solid state detector array and a one-dimensional collimator with one of convergent and divergent slats around a rotation axis in a plane parallel to a longitudinal axis of the subject while detecting photon emissions indicative of nuclear decay while wobbling the detector array and the collimator about the rotation axis to generate a plurality of one-dimensional projections of an examination region each at a plurality of angular orientations;

c) moving the detector array around the longitudinal axis of the subject and while repeating the step (b);

d) from the one-dimensional projections, generating second derivative data sets;

e) reconstructing the second derivative data sets into an image representation of the subject in the imaging region.

2. A method of diagnostic imaging comprising:

introducing a radioactive isotope into a subject located in an imaging region;

collimating the photon emissions with a focused slat collimator, the slats being tilted by a preselected angle from convergent on a symmetric focal spot;

rotating the collimator and a detector array with a planar radiation receiving face around an array rotation axis parallel to a normal to the radiation receiving face while detecting photon emissions to generate a plurality of one-dimensional projection data sets;

from the projection data sets generated with the detector array at 180° opposite positions generating first derivative data sets;

moving the collimator and the detector array around a longitudinal axis of the subject and while repeating the steps of rotating, collimating, and generating; and, reconstructing an image representation of the subject in the imaging region from the first derivative data sets.

3. The method as set forth in claim 2, further including:
while moving the collimator and the detector array around the longitudinal axis of the subject, wobbling the detector array.

4. The method as set forth in claim 3, further including:
wobbling the collimator and the detector array such that a focal spot of the collimator moves along a sinusoidal path.

5. The method as set forth in claim 4, further including:
wobbling the detector array at 180° opposite positions around the longitudinal axis.

6. The method as set forth in claim 2, further including:
changing an angle of the detector array with respect to the longitudinal axis as the detector moves around the longitudinal axis.

7. The method as set forth in claim 2, further including:
generating additional first derivative data sets with the detector array canted relative to the array rotation axis;
generating second derivative data sets from the first derivative data sets and the another first derivative data sets; and,
reconstructing the image representation from the second derivative data sets.

8. The method as set forth in claim 7, further including:
backprojecting the second derivative data sets in accordance with the Radon inversion formula to generate a three-dimensional image representation.

9. A diagnostic imaging apparatus comprising:
a detecting means for detecting radiation transmitted one of from and through a subject in an imaging region;
a collimating means with one of converging and diverging vanes mounted to the detecting means for collimating radiation detected by the detecting means;
a first rotating means for rotating and wobbling the detecting means and the collimating means about a rotation axis perpendicular to a longitudinal axis of the subject;
a second rotating means for rotating the detecting means and the collimating means about the longitudinal axis;
a means for generating derivative data sets from the radiation detected by the detecting means as the detecting means wobbles and rotates;
a means for reconstructing the derivative data sets into an image representation of the subject in the imaging region.

10. The diagnostic imaging apparatus as set forth in claim 9, wherein the collimating means includes convergent slats of a highly-attenuating material shifted by an angle α from a focal point perpendicular to a center of the detecting means.

11. The diagnostic imaging apparatus as set forth in claim 10 wherein the first rotating means rotates and wobbles the detecting means and the collimating means such that the focal spot follows a sinusoidal trajectory.

12. The diagnostic imaging apparatus as set forth in claim 10 wherein the means for generating derivative data sets includes:
a means for subtractively combining radiation detected with the detecting means and the collimating means wobbled to angular orientation in which the collimator focal point is offset to generate first derivative data sets;
a means for sorting the first derivative data sets into parallel planes;
a means for processing the parallel planes of first derivative data into the second derivative data sets.

13. The diagnostic imaging apparatus as set forth in claim 9, wherein the means for generating the derivative data sets includes:
a means for generating first derivative data set from the detected radiation; and
a means for generating second derivative data sets from the first derivative data sets.

14. A diagnostic imaging apparatus including:
a detector array which generates projection data in response to detected radiation;
a collimator with angled slats mounted to the detector array to collimate detected radiation such that the array generates planar projection data sets;
a means for rotating and wobbling the detector array and the collimator to obtain complimentary data sets which complimentary data sets generate first derivative data sets when subtracted;
a means for subtracting the complimentary data sets to generate first derivative data sets;
a means for generating a second derivative data sets from sets of the first derivative data sets;
a means for backprojecting the second derivative data sets into a volume image memory.

15. A SPECT camera comprising:
a detector head which is mounted for movement about an axis of a subject, the detector head including:
a linear array of detector elements mounted in the detector head for rotation about a detector axis of rotation and generating output signals,
a magnifying collimator having slats mounted between the detector elements of the array and angled to converge generally toward a focal point,
a means for rotating and wobbling the detector head around the detector axis of rotation such that the focal point follows an oscillating trajectory;
a means for combining the output signals from the linear array of detector elements as the focal point moves along the oscillating trajectory to generate first derivative data sets;
a means for generating second derivative data sets from the first derivative data sets;
a reconstruction processor which reconstructs the second derivative data sets into an image representation.

16. The camera as set forth in claim 15 wherein the slats are angled an angle α from converging precisely on the focal point, where α is greater than 0° and less than 5°.

17. A method of nuclear imaging comprising:
moving a linear detector array and a convergent collimator around a detector axis of rotation and around a subject axis of rotation and with a wobble that causes a focal point of the collimator to oscillate;
converting radiation from the subject which passes through the convergent collimator and is detected by the detector array into electrical signals;
subtracting electrical signals from the detector array generated at 180° opposite orientations around the detector axis to generate first derivative data sets;
generating second derivative data sets from first derivative data sets with the focal point oscillated;
reconstructing the second derivative data sets into a magnified volumetric image representation.

18. A method of nuclear imaging comprising:
stepping a linear detector array and a convergent collimator about a subject region of interest through a series of steps;

at each step, rotating and canting the detector array and the collimator relative to an axis perpendicular to a face of the detector;

converting radiation which passes through the collimator and is detected by the detector array into electrical signals;

generating first derivative data sets from the electrical signals;

generating second derivative data sets, each second derivative data set generated from a plurality of the first derivative data sets which are canted relative to each other;

backprojecting the second derivative data sets into a volumetric image representation.

19. The method as set forth in claim 18 further including:

shifting the detector axis of rotation during the rotating step.

20. The method as set forth in claim 18 further including:

orienting slats of the convergent collimator an angle $\alpha$ offset from a focal spot which lies on a perpendicular bisector of the collimator, the angle $\alpha$ being between 0° and 5°.

* * * * *